United States Patent
Mariadason et al.

(10) Patent No.: US 8,137,919 B2
(45) Date of Patent: Mar. 20, 2012

(54) METHOD OF DETERMINING THE SENSITIVITY OF CANCER CELLS TO EGFR INHIBITORS INCLUDING CETUXIMAB, PANITUMUMAB AND ERLOTINIB

(75) Inventors: John M. Mariadason, Balwyn (AU); Sanjay Goel, Syosset, NY (US)

(73) Assignee: Montefiore Medical Center, Bronx, NY (US)

( * ) Notice: Subject to any disclaimer, the term of this patent is extended or adjusted under 35 U.S.C. 154(b) by 371 days.

(21) Appl. No.: 12/384,826

(22) Filed: Apr. 8, 2009

(65) Prior Publication Data

US 2009/0258364 A1 Oct. 15, 2009

Related U.S. Application Data

(60) Provisional application No. 61/123,628, filed on Apr. 10, 2008.

(51) Int. Cl.
*C12Q 1/68* (2006.01)
(52) U.S. Cl. ..................................... 435/6.14
(58) Field of Classification Search ......................... None
See application file for complete search history.

(56) References Cited

U.S. PATENT DOCUMENTS

2006/0063824 A1* 3/2006 Kirkpatrick et al. .......... 514/422
2006/0147959 A1* 7/2006 Bell et al. .......................... 435/6

OTHER PUBLICATIONS

M. Frattini et al., PTEN loss of expression predicts cetuximab efficacy in metastatic colorectal . . . , British Journal of Cancer, Oct. 2007, pp. 1139-1145, vol. 97(8).
Katrien Berns et al., A Functional Genetic Approach Indentifies the PI3K Pathway . . . , Cancer Cell 12, Oct. 2007, pp. 395-402, Elesvier Inc.
F. Perrone et al., PI3KCA/PTEN deregulation contributes to impaired responses . . . , Annals of Oncology 20, Jul. 2008, pp. 84-90, Oxford University Press.
Andrea Sartore-Bianchi et al., PI3KCA Mutations in Colorectal Cancer Are Associated With . . . , Cancer Res 2009; 69: (5). Mar. 1, 2009, pp. 1851-1857.
Endoh H et al., entitled "PTEN and PIK3CA Expression Is Associated with Prolonged Survival after Gefitinib Treatment in EGFR-Mutated Lung Cancer Patients," Journal of Thoracic Oncology, vol. 1, No. 7, Sep. 2006, pp. 629-634.
Engelman J A et al., entitled "Allelic dilution obscures detection of a biologically significant resistance mutation in EGFR-amplified lung cancer", The Journal of Clinical Investigation, vol. 116, No. 10, Oct. 2006, pp. 2695-2706.
Jhawer M et al., entitled "PIK3CA Mutation/PTEN Expression Status Predicts Response of Colon Cancer Cells to the Epidermal Growth Factor Receptor Inhibitor Cetuximab," Cancer Res 2008; 68: (6), Mar. 15, 2008, pp. 1953-1961; Epub Mar. 13, 2008.
McKeage K, et al., entitled "Trastuzumab: a review of its use in the treatment of metastatic breast cancer overexpressing HER2," Drugs, 2002; 62(1); 209-43.
Borg A, et al., entitled "ERBB2 amplification in breast cancer with a high rate of proliferation," Oncogene, Jan. 1991;6 (1):137-43.
Heintz N H, et al., entitled "Amplification of the c-erb B-2 oncogene and prognosis of breast adenocarcinoma," Arch Pathol Lab Med, Feb. 1990;114(2):160-3.
Nathanson D R, et al., entitled "HER 2/neu expression and gene amplification in colon cancer," Int J Cancer, Jul. 20, 2003;105(6):796-802.
Miyakis S, et al., entitled "Differential expression and mutation of the ras family genes in human breast cancer," Biochem Biophys Res Commun, Oct. 20, 1998;251(2):609-12.
Sjoblom T, et al., entitled "The consensus coding sequences of human breast and colorectal cancers," Science, Oct. 13, 2006;314(5797):268-74.
Shak S, entitled "Overview of the trastuzumab (Herceptin) anti-HER2 monoclonal antibody clinical program in HER2-overexpressing metastatic breast cancer. Herceptin Multinational Investigator Study Group," Semin Oncol., Aug. 1999;26(4 Suppl 12):71-7.
Arnould L et al., entitled "Pathologic Complete Response to Trastuzumab-Based Neoadjuvant Therapy Is Related to the Level of HER-2 Amplification," Clin Cancer Res, 2007:13(21), Nov. 1, 2007, 6404-6409.
Borresen A.-L. et al., entitled "Amplification and protein over-expression of the neu/HER-2/c-erbB-2 protooncogene in human breast carcinomas: relationship to loss of gene sequences on chromosome 17, family history and prognosis," Br. J. Cancer (1990), 62, 585-590.
Borg A et al., entitled "HER-2/neu Amplification Predicts Poor Survival in Node-positive Breast Cancer," Cancer Research, 50, Jul. 15, 1990, 4332-4337.
Al-Kuraya K et al., entitled "HER2, TOP2A, CCND1, EGFR and C-MYC oncogene amplificaiton in colorectal cancer," J Clin Pathol, 2007;60:768-772.
Piccart-Gebhart M J et al., entitled Trastuzumab after Adjuvant Chemotherapy in HER2-Positive Breast Cancer, The New England Journal of Medicine, Oct. 20, 2005, vol. 353, No. 16, 1659-1672.
Romond E H et al., entitled "Trastuzumab plus Adjuvant Chemotherapy for Operable HER2-Positive Breast Cancer," The New England Journal of Medicine, Oct. 20, 2005, vol. 353, No. 16, 1673-1684.
Slamon D J et al., entitled "Use of Chemotherapy Plus a Monoclonal Antibody Against HER2 for Metastatic Breast Cancer that Overexpresses HER2," The New England Journal of Medicine, Mar. 15, 2001, vol. 344, No. 11, 783-792.

* cited by examiner

*Primary Examiner* — James Martinell
(74) *Attorney, Agent, or Firm* — Amster, Rothstein & Ebenstein LLP

(57) ABSTRACT

A method of determining if a cancer patient is amenable to treatment with EGFR inhibitors including but not limited to cetuximab, panitumumab or erlotinib by the following steps:
(a) Obtaining cells from a cancer patient's tumor;
(b) Determining if said cells contain a biomarker that is predictive of a therapeutic response to response to treatment with cetuximab or panitumumab. The biomarker is the mutation status of the PIK3CA gene and the expression status of the PTEN gene. Tumors that harbor activating mutations in Exon 9 and 20 of the PIK3CA gene or which show loss of PTEN protein expression will be considered not likely to benefit from EGFR targeting therapies.

11 Claims, 8 Drawing Sheets

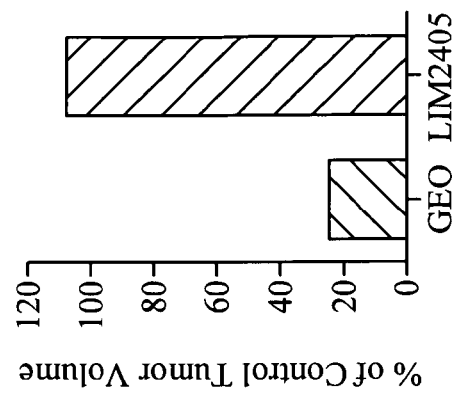
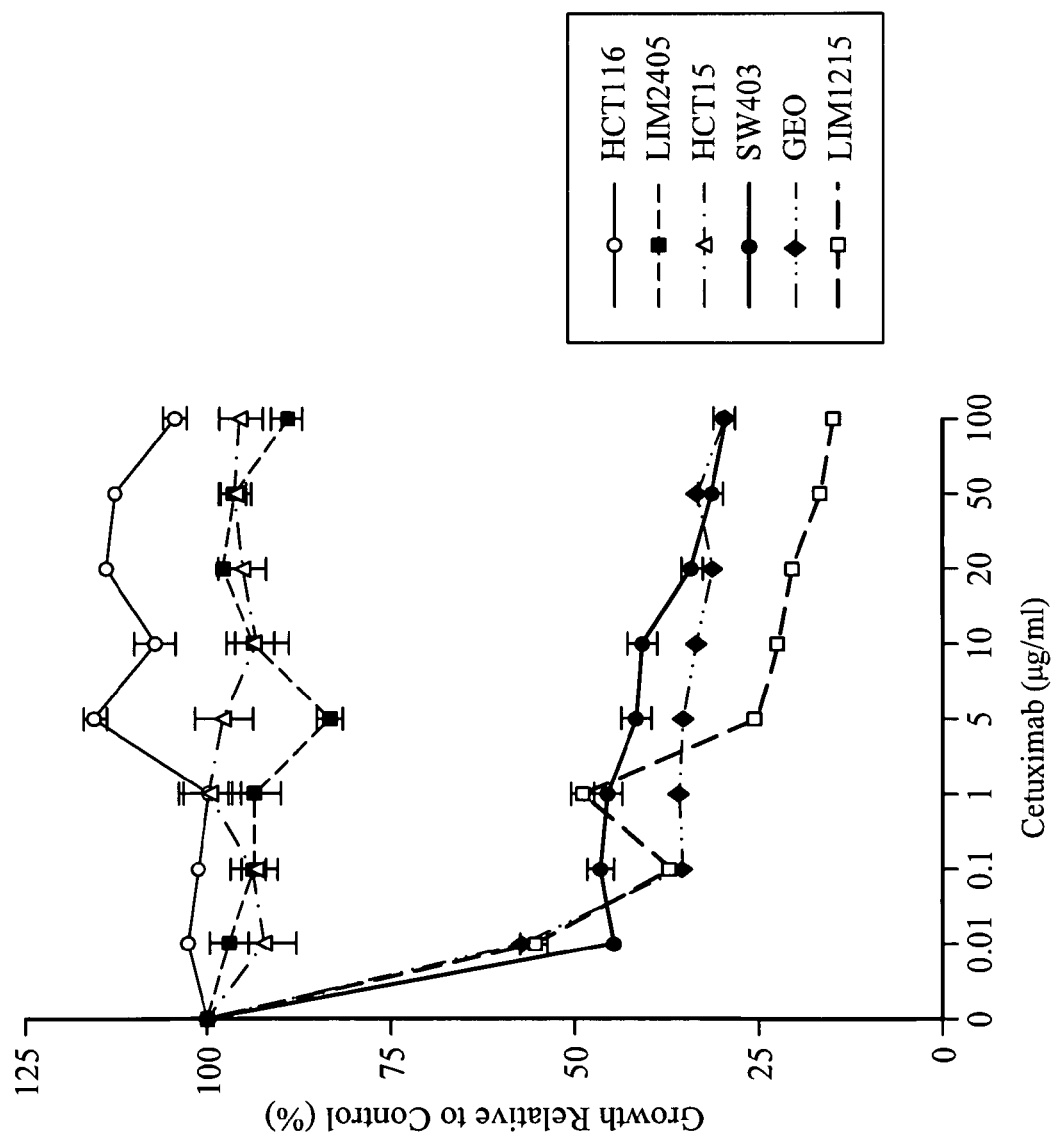
FIG. 2B
FIG. 2A

US 8,137,919 B2

METHOD OF DETERMINING THE SENSITIVITY OF CANCER CELLS TO EGFR INHIBITORS INCLUDING CETUXIMAB, PANITUMUMAB AND ERLOTINIB

CROSS-REFERENCE TO RELATED APPLICATIONS

This application claims the priority or Provisional Application Ser. No. 61/123,628, filed Apr. 10, 2008.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION

1. Field of the Invention

This invention is concerned with the determination of the sensitivity of a patient afflicted with cancer to the action of EGFR inhibitors including but not limited to cetuximab, erlotinib and panitumumab.

2. Description of Related Art

EGFR inhibitors such as Cetuximab and Panitimumab have efficacy for the treatment of colon cancer in some but not all patients. The present invention is directed to a screening test whereby tumor cells from a patient may be used to determine whether or not a colon cancer patient is a candidate for therapy with EGFR inhibitors.

BRIEF SUMMARY OF THE INVENTION

The invention is directed to a method of determining if a colon cancer patient is amenable to treatment with EGFR inhibitors such as cetuximab or panitumumab. The method comprises the following steps:
(a) Obtaining cells from a colon cancer patient's tumor;
(b) Determining if said cells contain a biomarker that is predictive of a therapeutic response to response to treatment with EGFR inhibitors. This biomarker is the mutation status of the PIK3CA gene and the mutation/expression status of the PTEN gene. Patients with activating mutations in the PIK3CA gene OR inactivating mutations/loss of expression of the PTEN gene will be considered NOT likely to benefit from EGFR-targeting therapies.

A preferred manner of determining if the colon cancer cells will respond to treatment with cetuximab or panitumumab is to (a) isolate colon tumor DNA and tissue from a patient with colon cancer; (b) determining if the isolated DNA does or does not have a mutation in either the PIK3CA or PTEN genes that confers resistance to treatment with EGFR inhibitors; (c) determining if the isolated tumor tissue shows expression of the PTEN gene, and (d) selecting those patients whose colon cancer does NOT have a resistance conferring PIIK3CA mutation or loss of PTEN expression for treatment with these agents.

The method of the invention may also be applied to determine if a cancer patient with, for example lung, breast or other solid tumors, is a candidate for treatment with the above mentioned anti EGFR drugs or any other anti EGFR drugs or for the screening of drugs for anti EGFR activity.

BRIEF DESCRIPTION OF THE SEVERAL VIEWS OF THE DRAWINGS

FIG. 2. (A) Shown for simplicity are the 3 most sensitive and resistant cell lines of the 22 cell lines screened for cetuximab response. Values shown are the mean±SEM of n=3-5 experiments. (B) Differential sensitivity of colon cancer cells to cetuximab in vivo. $5 \times 10^6$ cells of the cetuximab sensitive (GEO) and resistant (LIM2405) colon cancer cell lines were injected in SCID mice. Once palpable tumors had formed animals were injected with cetuximab (10 mg/kg) or PBS (control), biweekly, for 2 weeks following which animals were sacrificed, tumors excised and tumor volume calculated.

DETAILED DESCRIPTION OF THE INVENTION

Figure 1:
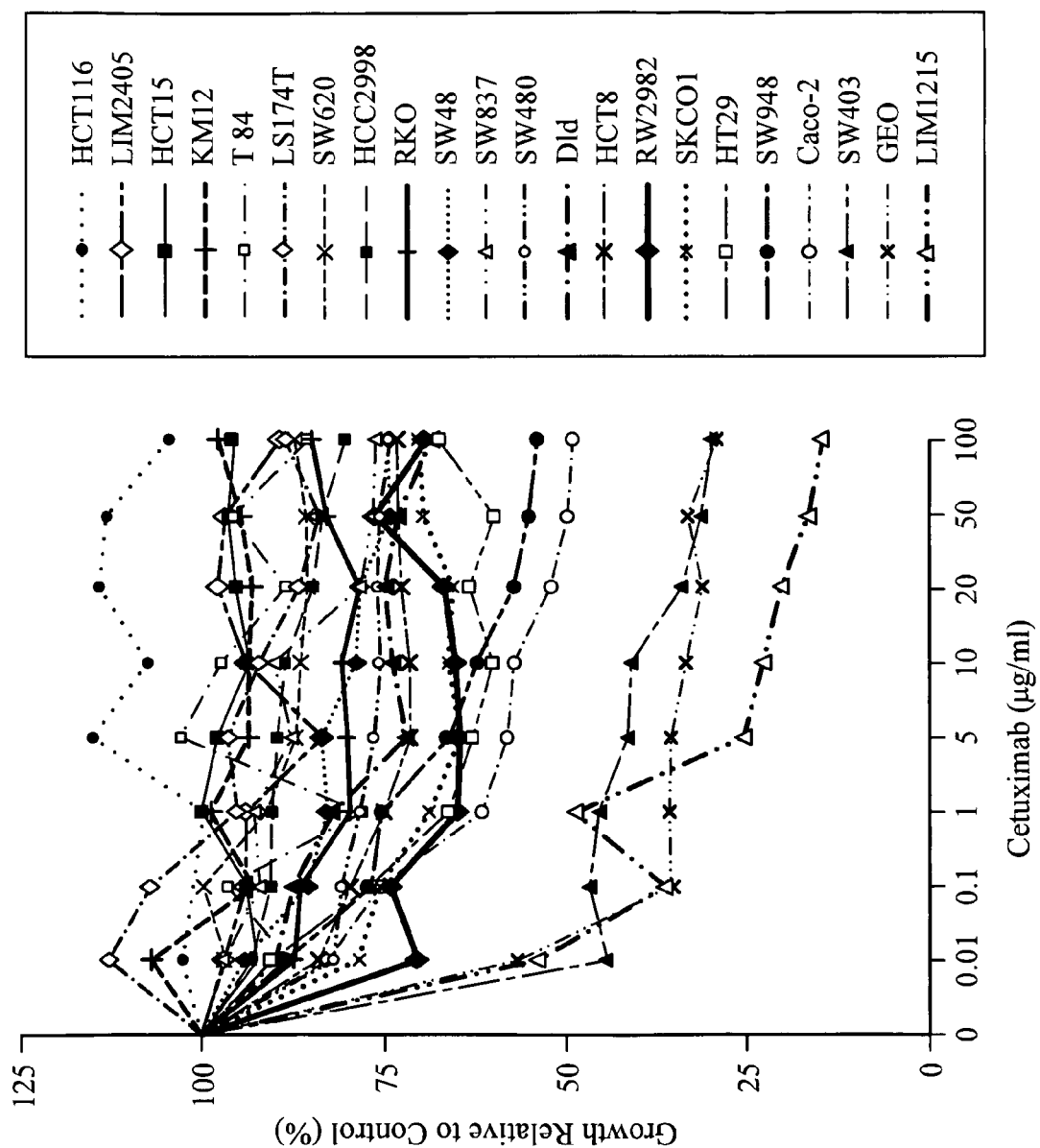
FIG. 1. Discloses differential sensitivity of colon cancer cell lines to 72 h cetuximab treatment. Shown are the response profiles of all 22 cell lines. Values shown are the mean±SEM of n=3-5 experiments. In the legend, cell lines are ordered in terms of increasing sensitivity to the 20 microgram/ml cetuximab concentration.

The EGFR signaling pathway is commonly activated in colorectal cancer, and has been explored for several years as a target for cancer therapy (1). EGFR is expressed in 30-85% of CRC's, and the intensity of its expression has been linked to reduced survival. Dysregulation of EGFR signaling has been shown to stimulate cell proliferation, angiogenesis and metastatic spread and to inhibit apoptosis. Activation of this pathway occurs following ligand (EGF, TGF, amphiregulin) binding to EGFR, which leads to EGFR phosphorylation and oligodimerization at the plasma membrane. This in turn triggers a chain of downstream signaling events that include activation of the Ras/Raf/mitogen-activated protein kinase (MAPK), phosphoinositide 3-kinase (PI3K)-Akt, and STAT pathways.

Several inhibitors of EGFR have recently been developed for the treatment of cancer including the small molecule EGFR inhibitors, tarveva (erlotinib) and Iressa (gefitinib) and the monoclonal antibodies, cetuximab and panitumumab. Cetuximab is a chimeric IgGI monoclonal antibody that targets the extra-cellular domain of EGFR, blocking ligand binding to the receptor. Based on a randomized phase II clinical trial, cetuximab was approved in the US in 2004 for use in combination with irinotecan, or as monotherapy in EGFR-positive irinotecan-refractory colorectal cancer. Cetuximab however has an objective response rate of only 9% when used as a single agent, along with toxicities of diarrhea, skin rash and infusion reactions. There is therefore a clear need for biomarkers predictive of response to cetuximab, in order to maximize likelihood of response while minimizing toxicities and cost.

One determinant of cetuximab sensitivity may be the presence of absence of mutations that result in constitutive activation of EGFR-mediated signaling. For example, in lung cancer, patients with activating mutations in the EGFR tyrosine kinase domain (encoded by exons 18-21) show significantly greater response to the small molecule inhibitors of EGFR tyrosine kinase activity, gefitinib and erlotinib. While mutations in the EGFR kinase domain are extremely rare in colon cancer, mutations which constitutively activate key signaling mediators downstream of EGFR, particularly the K-Ras/BRAF and PIK3CA/PTEN, are more common. Without being bound by any theory, the inventors believed that colon tumors with constitutively activated downstream signaling mediators of the EGFR pathway, particularly the PIK3CA/PTEN pathway would be refractory to inhibition of the pathway at the receptor level. Indeed, several recent studies have demonstrated a link between K-Ras mutation status and cetuximab response, with tumors WT for K-Ras showing improved response to this agent. However, other studies failed to do so.

The inventors observed that separation of cell lines according to PIK3CA and PTEN mutation status significantly distinguished cell lines according to cetuximab response. Therefore, a priori screening of colon tumors for PIK3CA and PTEN mutation status was applied as a means of identifying patients likely to benefit from this therapy.

DESCRIPTION OF THE PREFERRED EMBODIMENT

The following is a non-limiting Example of how the invention may be practiced.

Example

Determination of Sensitivity of Colon Cancer Cell Lines to Cetuximab and EGF:

Sensitivity of a panel of colon cancer cell lines to the EGFR inhibitors cetuximab and erlotinib and to the EGFR activator, EGF, were initially determined. The sources and maintenance of the colon cancer cell lines used in this study have been previously described, with the exception of the GEO cell line which was kindly provided by Dr. Z Fan (M. D. Anderson Cancer Center, TX). The colon cancer cell lines used to validate the method of the present invention are not required for the practice of the invention as the invention is intended to be used with colon cancer cells obtained from patients in conjunction with the diagnosis of the disease and the selection of a treatment regimen.

For determination of cetuximab and erlotinib sensitivity, 5000-50,000 cells per well were seeded in 96-well plates and treated with 0, 0.01, 0.1, 1, 5, 10, 20, 50, and 100 microgram/ml cetuximab for 72 h. For each cell line, one plate was harvested for determination of t=0 absorbance values. Viable cells were determined 72 h post-treatment using the MTT assay by measurement of absorbance at 570 nm. The relative rate of cell growth for each cell line was factored into the analysis by subtracting the absorbance at time zero from both the control and treatment groups. All the experiments were replicated a minimum of 3 times. For determination of sensitivity to EGF, cells were serum starved for 4 h then treated with 0, 0.5 or 5 ng/ml EGF for 24-72 h.

HCT116 PIK3CA Isogenic Cell Lines.

Isogenic HCT116 cells that were PIK3CA WT and mutant cells were generously provided by the Vogelstein/Velculescu laboratory.

Cell Cycle Distribution—Fluorescent Accelerated Cell Sorting (FACS) Analysis.

For assessment of the effect of cetuximab and EGF on cell cycle distribution, cells were stained with 50 micro g/ml propidium iodide overnight, and FACS analyses performed as previously described.

Determination of Cetuximab Response In Vivo.

For xenograft experiments, $5 \times 10^6$ GEO or LIM2405 cells in 200 microlitres of PBS/matrigel (1:1) were injected subcutaneously into the right flank of SCU) mice. Tumors were allowed to form for approximately 1 week. Animals were then injected with either PBS or cetuximab (10 mg/kg or approximately 300 microgram per mouse), intraperitoneally, biweekly for 2 weeks as previously described (28). Upon sacrifice, tumor volume was calculated from measurements of the smallest (s) and longest (1) diameter based on the following formula: Volume=$[(s^2 \times 1) \times \pi]/6$.

Identification of PIK3CA and PTEN Mutations in Colon Cancer Cell Lines.

The mutation status PIK3CA (Exon 9 and 20) and PTEN for a subset of the cell lines was obtained from the Wellcome Trust Sanger Institute Cancer Genome Project web site. For cell lines for which the mutation status of one or more of these genes was unknown, genomic DNA was isolated using the Qiagen DNA extraction kit. Primers used for amplification of Exon 9 of PIK3CA were F: GCTTTTTCTGTAAATCATCT-GTG (SEQ ID NO:1), and R: CTGAGATCAGCCAAAT-TCAGT (SEQ ID NO:2), for exon 20 of PIK3CA were, F: CATTTGCTCCAAACTGACCA (SEQ ID NO:3) and R: TACTCCAAAGCCTCTTGCTC (SEQ ID NO:4) (for codon 1023 mutation) and F: ACATTCGAAAGACCCTAGCC (SEQ ID NO:5) and R: CAATTCCTATGCAATCGGTCT (SEQ ID NO:6) (for codon 1047 mutation). PTEN expression status was determined by western blot, using an anti-PTEN antibody (Cell Signaling). Cell lines lacking PTEN expression were considered PTEN mutant.

Statistical Analyses.

Differences between groups was analyzed using an unpaired student's t test with p<0.05 considered statistically significant. Differences in cetuximab sensitivity between cell lines wild type or mutant for PIK3CA/PTEN was determined using an unpaired student's t test. For correlative analyses, a Pearson's correlation coefficient was computed with P<0.05 considered statistically significant.

Results

Determination of Sensitivity of Colon Cancer Cell Lines to Cetuximab.

To identify colon cancer cell lines with differential response to cetuximab, a panel of 22 colon cancer cell lines was screened for cetuximab response using the MTT assay. As shown in FIG. 1, a spectrum of sensitivity to cetuximab was identified. Maximal response was observed in the LIM1215, GEO and SW403 cell lines, where growth was inhibited >70% at the maximum concentration of cetuximab tested. An intermediate response (approximately 50% growth inhibition), was observed in the Caco-2 and SW948 cell lines while minimal response (<35% growth inhibition) was observed in the remaining cell lines (FIG. 1 and FIG. 2).

Differential Sensitivity of Colon Cancer Cell Lines to Cetuximab In Vitro is Also Observed In Vivo.

To confirm the differential sensitivity of colon cancer cell lines to cetuximab in vivo, the sensitive GEO, and resistant LIM2405, cell lines were grown as xenografts in SCID mice and treated with 10 mg/kg cetuximab biweekly for 2 weeks. Consistent with the in vitro findings, cetuximab inhibited growth of GEO cells by approximately 75% (205±36 mm$^3$ compared to 854±201 mm$^3$ in cetuximab treated and control mice respectively), whereas no growth inhibitory effect was observed in LIM2405 cells (999±32 mm$^3$ versus 934±66 mm$^3$ in cetuximab treated and control mice respectively). (FIG. 2B).

Comparable Sensitivity Profiles of Colon Cancer Cells to Cetuximab and Erlotinb.

Figure 3B:
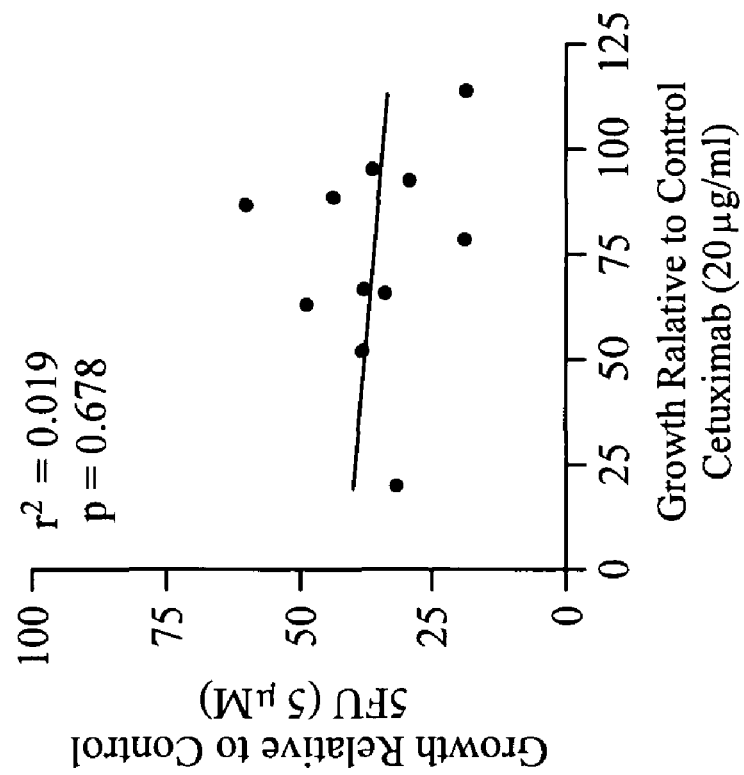
FIGS. 3A and 3B, demonstrate the correlation of response between cetuximab and erlotinib, and cetuximab and 5FU, respectively. To obtain these correlations 12 colon cancer cell lines (LIM1215, GEO, Caco-2, HT29, SKCO-1, RW2982, RKO, LS174T, T84, KM12, HCT15 and HCT116) were treated with (A) 5 microgram/ml of erlotinib, or (B) 5 mM 5-FU for 72 hours, and cell growth determined by MTT assay. Correlation of response between cetuximab and erlotinib and between cetuximab and 5FU was determined by computation of a Pearson's correlation coefficient.
Figure 3A:
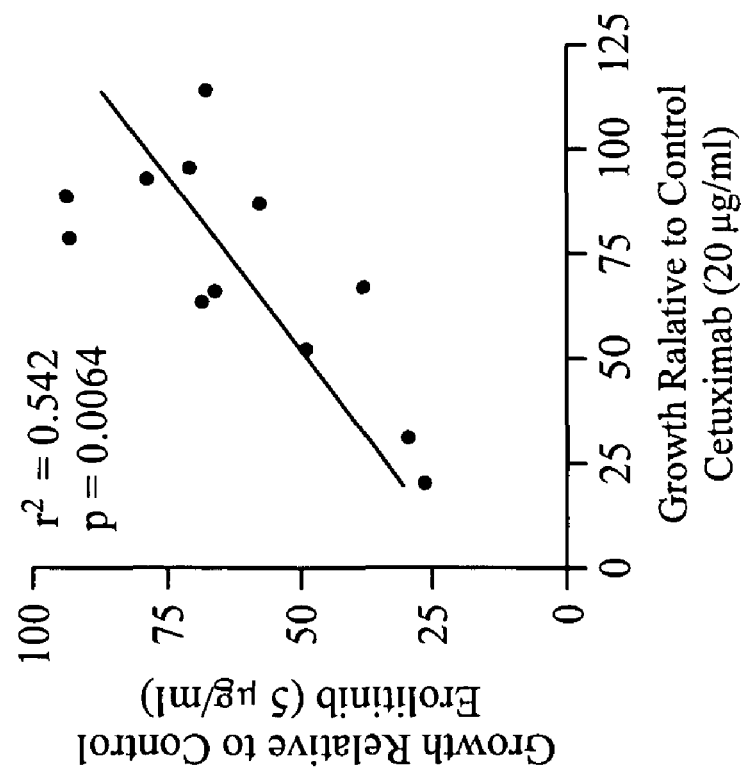

To confirm that the sensitivity spectrum of colon cancer cells to cetuximab reflected inhibition of EGFR and its downstream signaling pathway, we assessed the response of 12 of the cell lines to erlotinib (5 microgram/ml), a small molecule tyrosine kinase inhibitor that targets the intracellular domain of EGFR. As shown in FIG. 3A, a significant correlation between response of colon cancer cell lines to cetuximab and erlotinib was observed, consistent with both agents mediating growth inhibition through inhibition of EGFR signaling ($r^2$=0.542, p=0.006). In contrast, no significant correlation was observed between cetuximab response and response to the mechanistically distinct chemotherapeutic agent, 5FU ($r^2$=0.019, p=0.678, FIG. 3B).

Cetuximab Induces a $G_0/G_1$ Arrest in Colon Cancer Cells.

Figure 4A:
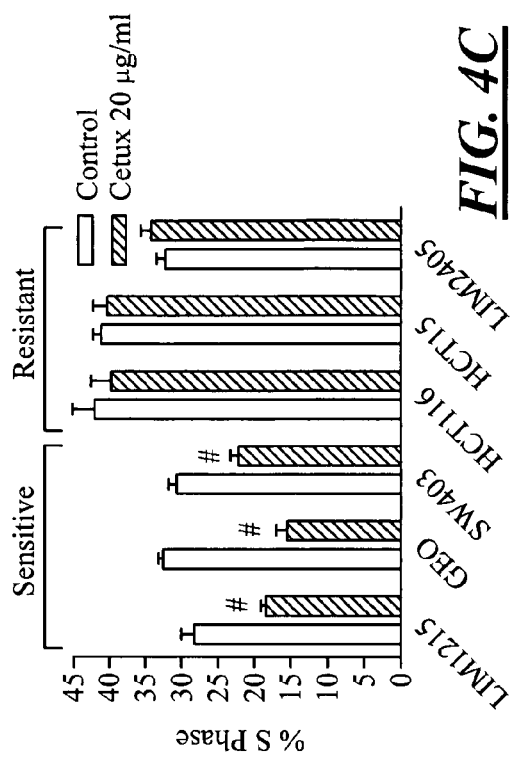
FIG. 4. Discloses a summary of cell cycle analysis of cetuximab sensitive (GEO, LIM1215, SW403) and resistant (LIM2405, HCT116, HCT15) colon cancer cell lines. For assessment of cell cycle distribution, cells were treated for 24 hours with 20 microgram/ml cetuximab (A-C). For assessment of apoptosis, cells were treated with 20 microgram/ml cetuximab or 5 micro Molar 5FU for 72 h (D). Cell cycle distribution and apoptosis was assessed by PI staining and FACS analysis. Values shown are mean±SEM, n=3, #P<0.05.
Figure 4B:
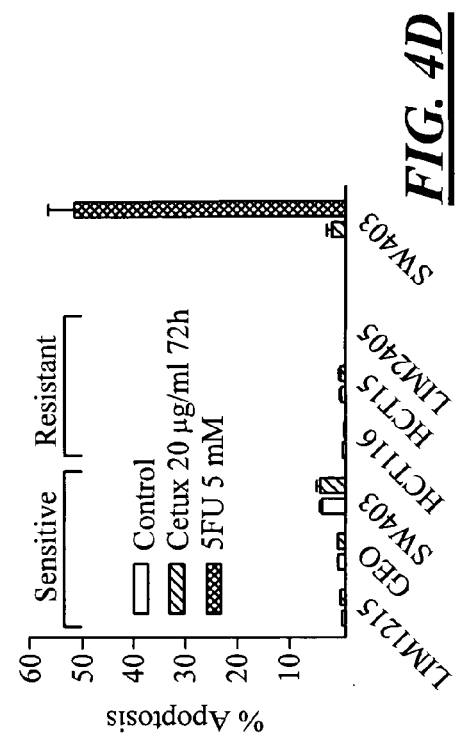
Figure 4C:
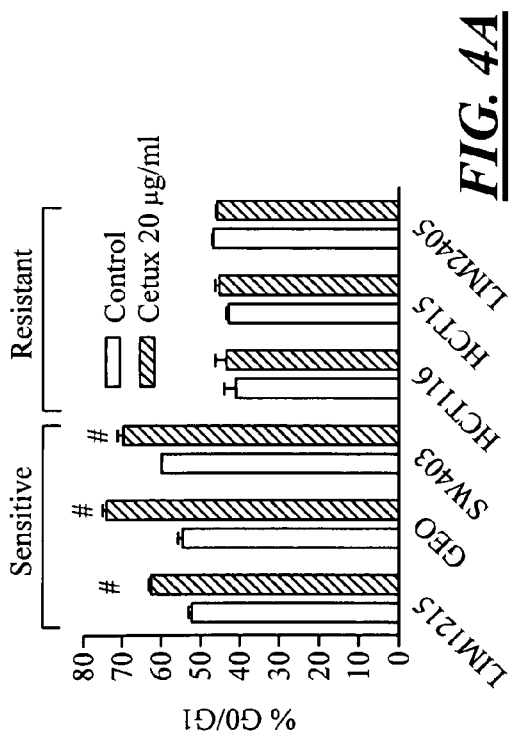
Figure 4D:
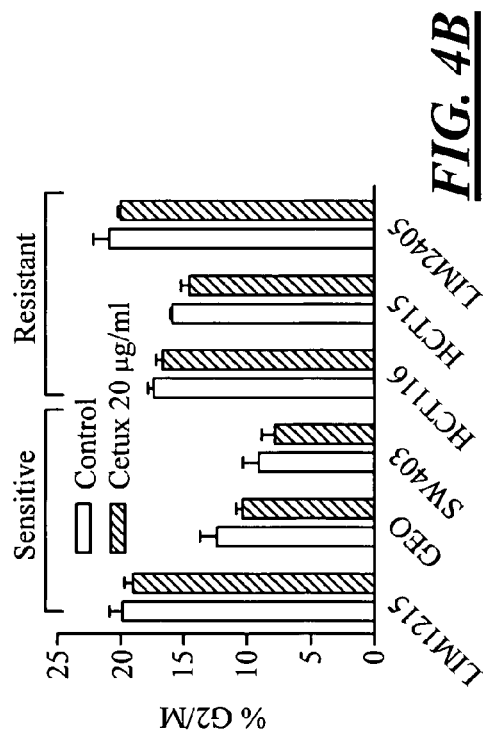

To confirm the findings of the MTT assay, and to further assess the effect of cetuximab on cell cycle distribution, we determined the effect of cetuximab on cell cycle distribution in the 3 most sensitive and 3 most resistant cell lines (FIG. 4A-C). Consistent with the MTT data, an increase in the percentage of cells in $G_0/G_1$ and a concomitant decrease in the percentage of cells in S phase was observed in the 3 sensitive cell lines (LIM1215, GEO and SW403). No difference in the percentage of cells in $G_2/M$ was observed. In comparison, minimal change in cell cycle distribution was observed in the resistant cell lines (LIM2405, HCT116 and HCT15). Importantly, minimal effects on apoptosis were observed in this cell line panel either at 24 or 72 hours following cetuximab treatment (FIG. 4D), indicating cetuximab elicits a predominantly cytostatic effect in colon cancer cells. In contrast, treatment of SW403 cells with 5 microMolar 5-fluoruracil induced approximately 50% apoptosis following 72 hours treatment, demonstrating that these cell lines are not inherently resistant to apoptosis (FIG. 4D).

Mutation Status of PIK3CA and/or PTEN Predicts Response to Cetuximab.

Ligand binding to EGFR results in signal transduction via the Ras/Raf/MEK/MAPK and the PI3K/AKT pathway. As mutations that result in constitutive activation of each of these pathways occur at high frequencies in colon cancer, we hypothesized that colon cancer cell lines with constitutively activated signaling downstream of EGFR would not be dependent on ligand binding to EGFR for their growth, and in turn, would be refractory to cetuximab.

Mutation driven constitutive activation of the PI3K signaling pathway has been reported to occur in approximately 30% of colon tumors, primarily due to activating mutations in exons 9 and 20 of the PIK3CA gene (18), and to a lesser extent due to inactivating PTEN mutations or PTEN promoter methylation (29). The presence of activating PIK3CA mutations in the cell line panel was assessed by literature searches, from the COSMIC database and by direct sequencing of exons 9 and 20 of the PIK3CA gene. Mutations in PIK3CA were identified in 8 of the 22 cell lines (Table 1, FIG. 5). PTEN is a tumor suppressor that acts as a negative regulator of PI3K signaling by converting $PIP_3$ to $PIP_2$, and truncating mutations which result in loss of PTEN expression have been reported in approximately 20% of MSI colon cancers. We noted that the KM12 cell line that was PIK3CA wild type yet highly resistant to cetuximab, harbors a truncating mutation in PTEN (Wellcome Trust Sanger Institute Cancer Genome Project, www.sanger.ac.uk/genetics/CGP). The PTEN expression status of the cell line panel was therefore determined by western blot. In addition to KM12, loss of PTEN expression was also observed in the cetuximab resistant LIM2405 line. Consistent with previous reports, both lines with loss of PTEN expression were derived from MSI colon cancers. Furthermore, the occurrence of PIK3CA mutations and loss of PTEN expression in the cell line was mutually exclusive as previously reported (32).

Figure 7B:
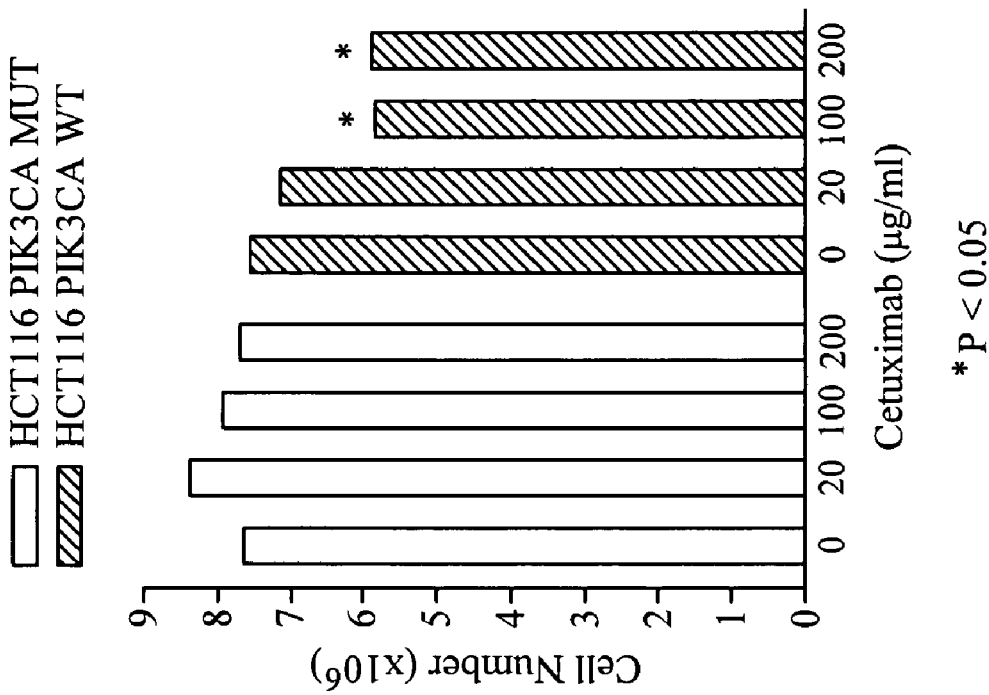
FIG. 7A: Discloses mutation status and response to cetuximab in vitro where the Cetuximab response in the 22 colon cancer cell line panel is separated according to PIK3CA mutation/PTEN expression status (*p=0.008) and FIG. 7B Reports the Cetuximab response in isogenic PIK3CA mutant and WT HCT116 cell lines. Cells were serum starved overnight then treated with 20 or 100 microgram/ml cetuximab for 24 h in medium containing 0.5% serum. Differential sensitivity was assessed by direct counting of cell number. Cetuximab response was determined 24 h post treatment by counting cell number.
Figure 7A:
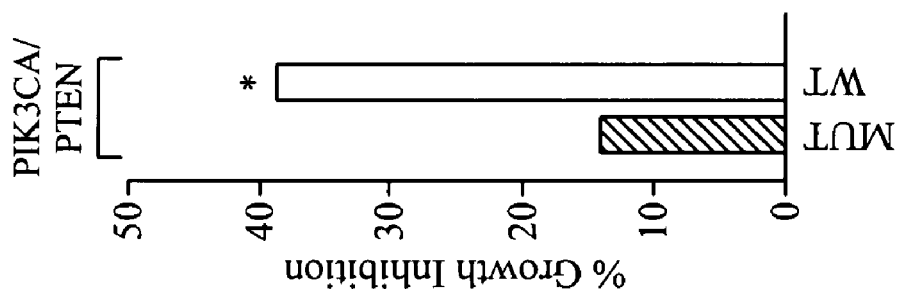

Separation of cell lines according to PIK3CA mutation and/or PTEN expression status identified a significant difference in cetuximab sensitivity, with PIK3CA mutant/PTEN null cell lines being significantly more refractory to cetuximab treatment (14.0±5.0% versus 38.5±6.4% growth inhibition for PIK3CA mutant/PTEN null versus PIK3CA WT/PTEN expressing cell lines respectively, p=0.008, FIG. 7A).

To further confirm this finding, we examined cetuximab response in a pair of isogenic HCT116 cells provided by the Velculescu/Vogelstein laboratories, in which either the mutant or WT PIK3CA allele has been deleted by homologous recombination (26). While the PIK3CA mutant HCT116 isogenic cell line was highly resistant to cetuximab, a modest though statistically significant response to cetuximab was observed in the PIK3CA WT isogenic line (FIG. 6B). Collectively, these findings demonstrate that colon cancer cell lines with constitutively active PI3K signaling are refractory to cetuximab.

Cetuximab Sensitivity Correlates with Growth Response to EGF

Signaling via the EGFR receptor is initiated upon ligand binding (EGF, TGFalpha, amphiregulin), with signal transduction primarily through the PTEN/PI3K/AKT and/or Ras/Raf/MEK/ERK pathways. We speculated therefore, that cell lines responsive to ligand mediated canonical activation of this pathway for their growth would be most sensitive to cetuximab.

Figure 5A:
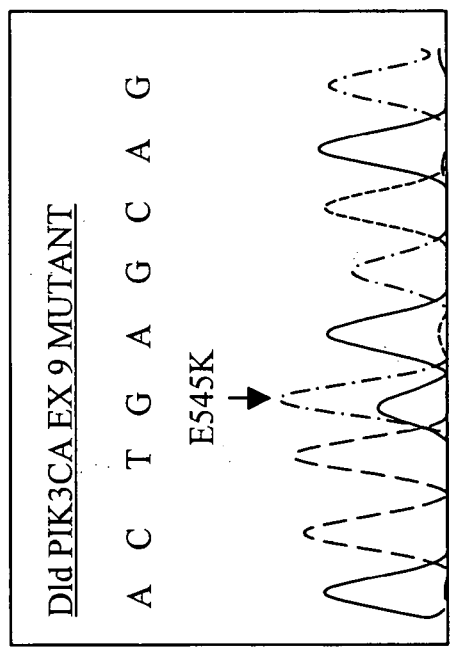
FIG. 5A. Discloses chromatograms depicting sequencing results of mutated genes which cause resistance to cetuximab and panitumumab in colon cancer cell lines. The right panel shows a PIK3CA mutation.
Figure 5B:
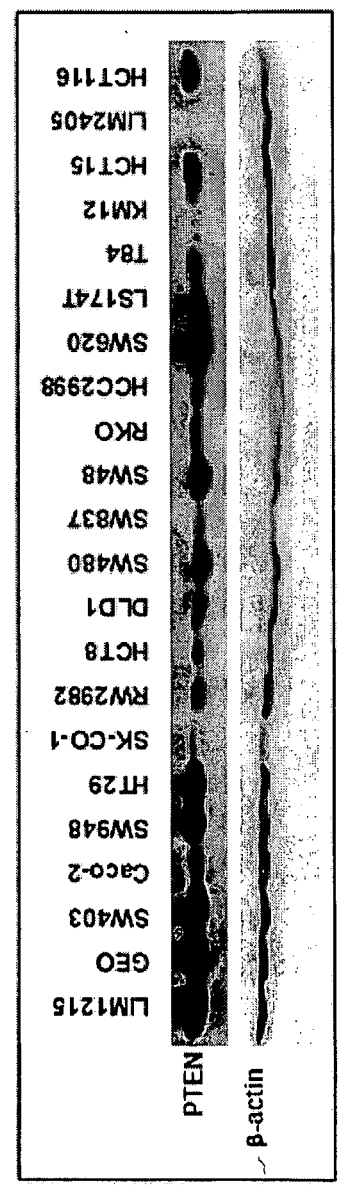
FIG. 5B shows inactivation and loss of expression of the PTEN gene as assessed by western blotting.
Figure 6A:
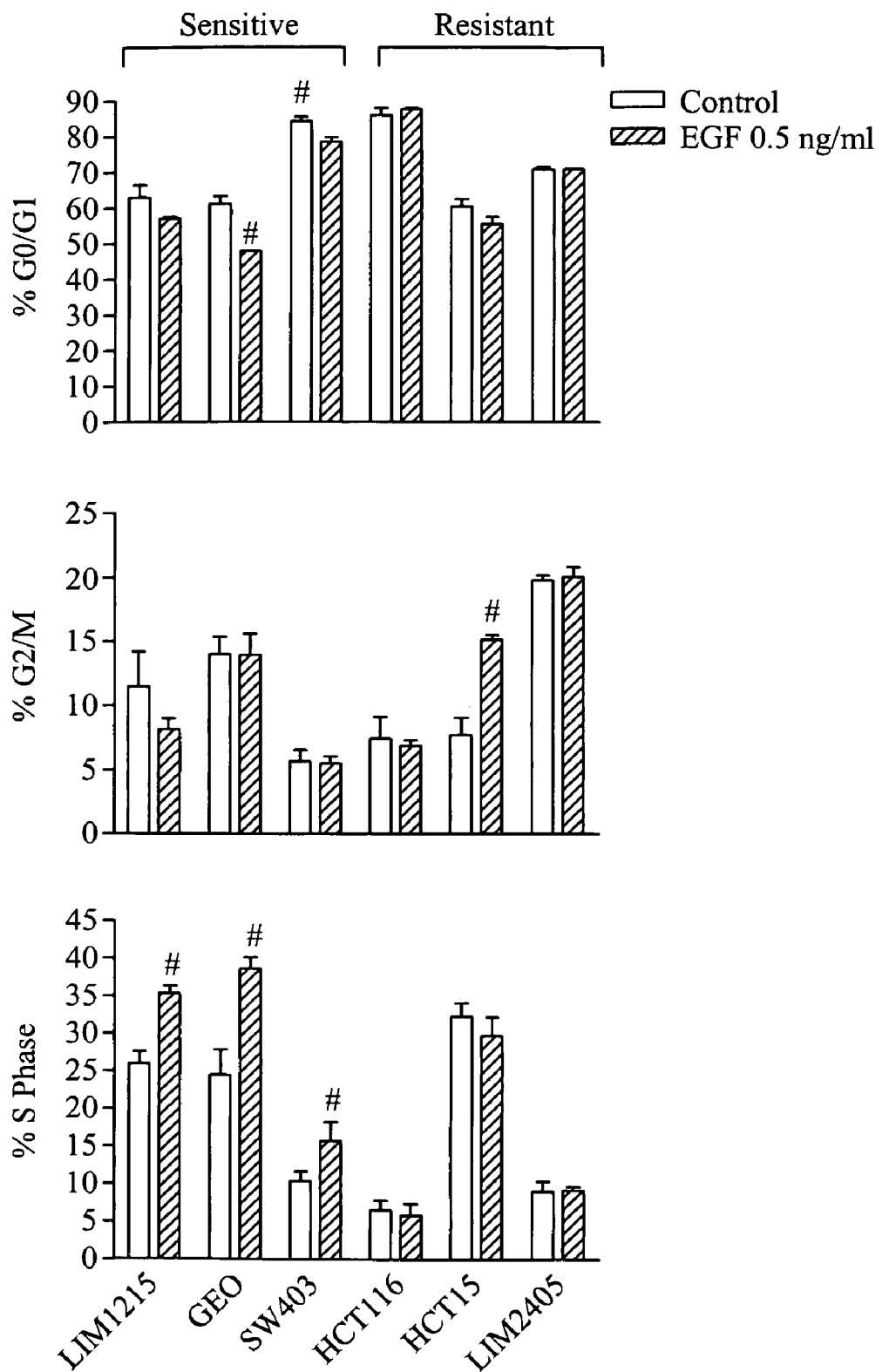
FIG. 6A Discloses EGF selectively stimulates cell growth in cetuximab sensitive cell lines.
Figure 6B:
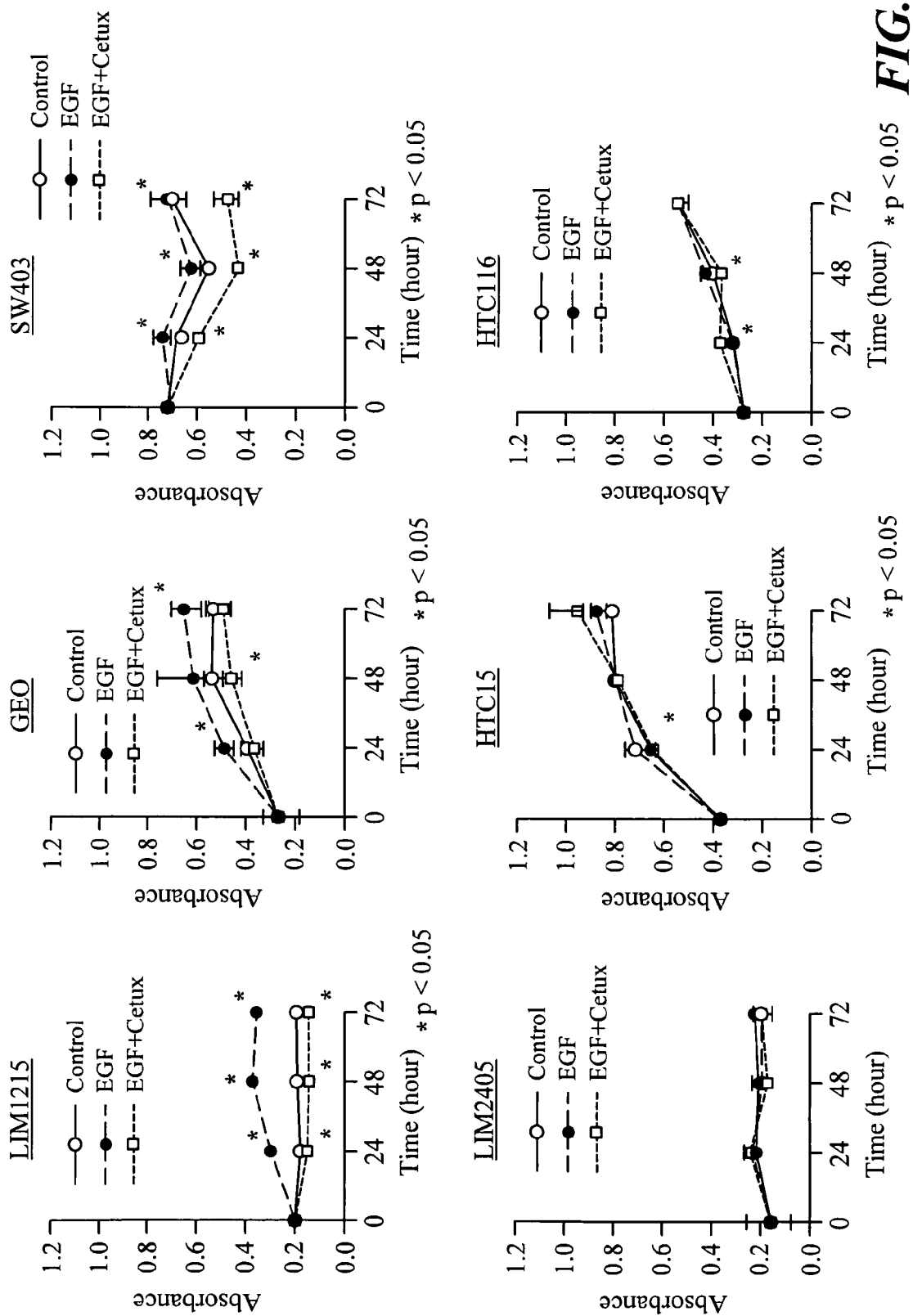
FIG. 6B shows the results of testing the three most cetuximab sensitive and resistant cell lines were treated for 24-48 hours with 5 ng/ml EGF or left untreated (control). Cell growth was assayed by MTT assay. Values shown are mean±SEM from a representative experiment, #p<0.05. Experiments were repeated 3 separate times.

To test this, the proliferative response of the 3 most cetuximab-sensitive and 3 most cetuximab-resistant cell lines to exogenous EGF-treatment was examined under serum-free conditions (FIG. 6). A significant increase in S-phase was observed 24 h post EGF treatment (0.5 ng/ml) in the 3 cetuximab sensitive cell lines, GEO, LIM1215, and SW403, but not in the 3 most cetuximab resistant cell lines, LIM2405, HCT15, and HCT116 (FIG. 6A). To confirm this result we also performed MTT assays. Treatment with 0.5 or 5 ng/ml EGF preferentially increased growth of the cetuximab sensitive cell lines, establishing a clear link between response to the mitogenic effects of EGF and the growth inhibitory effects of cetuximab (FIG. 5). In additional validation experiments we demonstrated that pre-treatment of the EGF responsive cell lines with cetuximab significantly attenuated the mitogenic effect of EGF. These findings indicate that a subset of colon tumors exist that are dependent upon ligand activation of EGFR for their growth, and it is these cell lines that are growth inhibited by blockade of ligand binding to the EGFR.

As recently demonstrated, tumor cells can lose their dependence on growth factors via mutation driven, constitutive activation, of signaling pathways downstream of growth factor receptors, specifically the PI3 kinase and Ras/MAPK pathways. We observed that stratification of cell lines according to PIK3CA/PTEN mutation status identified a significant difference in cetuximab response, with PIK3CAiPTEN mutant lines being consistently more resistant to this agent compared to wild type lines. This finding was further confirmed using the HCT116 PIK3CA WT and mutant isogenic cell lines, where increased sensitivity to cetuximab was observed in the PIK3CA WT line. This finding is consistent with the reported observation that HCT116 PIK3CA WT cells are more dependent on serum derived growth factors for their growth, and are more responsive to EGF ligand induced signaling compared to the mutant line. Collectively, these findings imply that colon cancer cell lines which acquire mutations that result in constitutive activation of the PI3K pathway have a diminished dependence on canonical EGFR ligand-induced signaling for their growth, and are, therefore, more resistant to EGFR-targeted therapies.

Consistent with the present findings, Frattini et al, (Br J Cancer 2007; 97:1139-45) recently reported that colon tumors with loss of PTEN expression have significantly reduced response to cetuximab. Likewise, breast cancers with either activating mutations in PIK3CA or with loss of PTEN expression respond poorly to treatment with the Her2/Neu targeting antibody, trastuzumab. Collectively, these studies provide additional clinical evidence that the mutation status of the PI3K signaling pathway should be considered prior to treatment with EGF receptor family antagonists.

Importantly, while cell lines with mutations in PIK3CA/PTEN were consistently resistant to cetuximab, not all cell, lines wild type at the four loci tested, were sensitive to cetuximab. A possible mechanism of resistance to cetuximab of these cell lines may be the existence of mutations in the Ras/BRAF signaling pathway or alternate mutations in the PIK3CA/PTEN pathway, other than those screened for in the present analysis. For example, with regards to the PI3K pathway, less frequently occurring mutations have been described in exons 1 and 2 of PIK3CA which encode the p85 interacting domain. Mutations in p85alpha(47), PDK1, AKT2, PAK4, and INSRR, as well as amplifications in AKT2 and IRS2 have also been described, as have less frequently occurring mutations in codon 146 (A146T) of the K-Ras gene. In this regard, it is notable that mutations in both codon 146 of K-Ras, and in p85alpha have been reported in the relatively resistant HCC2998 cell line (48, 49), which is wild type at the 4 hot spot loci examined in the present analysis.

In conclusion, we have discovered that cell lines responsive to canonical EGFR signaling-mediated growth are also responsive to cetuximab. We observed that cell lines mutant for PIK3CA/PTEN are significantly more resistant to cetuximab compared to PIK3CA/PTEN wild type lines. Determination of the mutation status of signaling mediators downstream of EGFR, specifically in the PIK3CA/PTEN pathway may help stratify patients likely to benefit from EGFR inhibitors, including cetuximab, panitumumab and erlotinib.

Table 1 provides data which: correlates PIK3CA mutation/PTEN expression status of cell lines and response to cetuximab.

TABLE 1

| Cell line | % Inhibition relative to control (Mean ± SEM) | Mutant PIK3CA Ex 9 | Mutant PIK3CA Ex 20 | Mutant Total PIK3CA | PTEN Null | Mutant PIK3CA/PTEN |
|---|---|---|---|---|---|---|
| LIM1215 | 79.6 ± 3.5 | | | | | |
| GEO | 68.7 ± 1.6 | | | | | |
| SW403 | 66.0 ± 4.9 | | | | | |
| CAC02 | 47.7 ± 4.3 | | | | | |
| SW948 | 42.7 ± 1.4 | + | | + | | + |
| HT29 | 36.5 ± 8.2 | | | | | |
| SKCO1 | 33.9 ± 3.5 | | | | | |
| RW2982 | 33.0 ± 1.3 | | | | | |
| HCT8 | 27.1 ± 4.0 | + | | + | | + |
| DLD | 24.9 ± 7.4 | + | | + | | + |
| SW480 | 23.7 ± 3.0 | | | | | |
| SW837 | 21.8 ± 8.5 | | | | | |
| SW48 | 21.8 ± 1.2 | | | | | |
| RKO | 21.2 ± 6.9 | | + | + | | + |
| HCC2998* | 15.2 ± 3.3 | | | | | |
| SW620 | 14.5 ± 2.2 | | | | | |
| LS174T | 13.0 ± 3.9 | | + | + | | + |
| T84 | 11.2 ± 9.2 | + | | + | | + |
| KM12 | 7.1 ± 9.1 | | | | + | + |
| HCT15 | 4.5 ± 6.5 | + | | + | | + |
| LIM2405 | 2.0 ± 2.2 | | | | + | + |
| HCT116 | −14.1 ± 1.3 | | + | + | | + |

The invention claimed is:

1. A method of determining if a cancer patient is amenable to treatment with an EGFR inhibitor which comprises determining the mutation status of the PIK3CA gene in a tumor from the cancer patient, wherein an activating mutation in the PIK3CA gene is indicative that the patient is not likely to benefit from treatment with the EGFR inhibitor.

2. The method of claim 1, wherein the activating mutation is in exon 9 of the PIK3CA gene.

3. The method of claim 1, wherein the activating mutation is in exon 20 of the PIK3CA gene.

4. The method of claim 1, wherein the activating mutation is in both exon 9 and exon 20 of the PIK3CA gene.

5. The method of claim 1, wherein the tumor is a solid tumor.

6. The method of claim 1, wherein the tumor is a colon tumor, a lung tumor, a breast tumor or a gastric tumor.

7. The method of claim 1, wherein the EGFR inhibitor is a small molecule or a monoclonal antibody.

8. The method of claim 1, wherein the EGFR inhibitor is cetuximab, erlotinib, gefitinib or panitumumab.

9. The method of claim 1, which comprises selecting a patient who does not have an activating mutation in the PIK3CA gene for therapy with an EGFR inhibitor.

10. The method of claim 1, wherein the mutation status of the PIK3CA gene is determined by isolating DNA from cells isolated from the tumor and determining if the DNA has a mutation in the PIK3CA gene.

11. The method of claim 1, which comprises selecting a patient who does have an activating mutation in the PIK3CA gene for therapy with a cancer therapeutic that is not an EGFR inhibitor.

* * * * *

SEQUENCE LISTING

<160> NUMBER OF SEQ ID NOS: 6

<210> SEQ ID NO 1
<211> LENGTH: 23
<212> TYPE: DNA
<213> ORGANISM: Artificial
<220> FEATURE:
<223> OTHER INFORMATION: forward primer for exon 9 of PIK3CA

<400> SEQUENCE: 1 gcttttttctg taaatcatct gtg          23

<210> SEQ ID NO 2
<211> LENGTH: 21
<212> TYPE: DNA
<213> ORGANISM: Artificial
<220> FEATURE:
<223> OTHER INFORMATION: reverse primer for exon 9 of PIK3CA

<400> SEQUENCE: 2
ctgagatcag ccaaattcag t          21

<210> SEQ ID NO 3
<211> LENGTH: 20
<212> TYPE: DNA
<213> ORGANISM: Artificial
<220> FEATURE:
<223> OTHER INFORMATION: forward primer for exon 20 of PIK3CA (codon
      1023 mutation)

<400> SEQUENCE: 3
catttgctcc aaactgacca          20

<210> SEQ ID NO 4
<211> LENGTH: 20
<212> TYPE: DNA
<213> ORGANISM: Artificial
<220> FEATURE:
<223> OTHER INFORMATION: reverse  primer for exon 20 of PIK3CA (codon
      1023 mutation)

<400> SEQUENCE: 4
tactccaaag cctcttgctc          20

<210> SEQ ID NO 5
<211> LENGTH: 20
<212> TYPE: DNA
<213> ORGANISM: Artificial
<220> FEATURE:
<223> OTHER INFORMATION: forward primer for codon 1047 mutation of
      PIK3CA

<400> SEQUENCE: 5
acattcgaaa gaccctagcc          20

<210> SEQ ID NO 6
<211> LENGTH: 21
<212> TYPE: DNA
<213> ORGANISM: Artificial
<220> FEATURE:
<223> OTHER INFORMATION: reverse primer for codon 1047 mutation of
      PIK3CA

<400> SEQUENCE: 6
caattcctat gcaatcggtc t          21